(12) United States Patent
Ford et al.

(10) Patent No.: US 6,733,982 B1
(45) Date of Patent: May 11, 2004

(54) METHOD FOR SCREENING COMPOUNDS FOR ALPHA$_{1B}$ ADRENERGIC RECEPTOR ANTAGONIST AND ANALGESIC ACTIVITY

(75) Inventors: Anthony P. D. W. Ford, Mountain View, CA (US); Timothy James Williams, Sunnyvale, CA (US); Kathleen Ruth Gogas, Los Banos, CA (US); Lupita O. Jacobson, Cupertino, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/520,584

(22) Filed: Mar. 8, 2000

Related U.S. Application Data

(60) Provisional application No. 60/124,721, filed on Mar. 17, 1999.

(51) Int. Cl.$^7$ .......................... C07K 1/00; C07H 21/04; C12N 1/20; C12P 21/06; G01N 33/566
(52) U.S. Cl. .......................... 435/7.21; 435/6; 435/7.1; 435/69.1; 435/69.5; 435/252.3; 436/501; 514/2; 514/260; 530/350; 536/23.5; 544/284; 544/291
(58) Field of Search .......................... 435/6, 7.1, 7.21, 435/69.1, 69.5, 252.3; 514/2, 260; 530/350; 544/284, 291; 536/23.5; 436/501

(56) References Cited

U.S. PATENT DOCUMENTS

| | | |
|---|---|---|
| 5,403,847 A | 4/1995 | Gluchowski et al. |
| 5,556,753 A | 9/1996 | Bard et al. |
| 5,578,611 A | 11/1996 | Gluchowski et al. |
| 5,595,880 A | 1/1997 | Weinshank et al. |
| 5,610,174 A | 3/1997 | Craig et al. |
| 5,714,381 A | 2/1998 | Bard et al. |
| 5,780,485 A | 7/1998 | Gluchowski et al. |
| 5,859,014 A | 1/1999 | Bantle et al. |

OTHER PUBLICATIONS

Acosta–Martinez et al., Neurochemistry International 35(383–391)1999.*
Martin et al., J. Pharm. Exp. Ther. 282(228–235)1997.*
Stevens et al., Regional anesthesia 18:318–321, 1993.*
Galer et al., PAIN, 50:205–208, 1992.*
Xie et al., Society for Neuroscience Abstracts, 24(2)2089, Nov. 7, 1998.*
Hanft et al. British Journal of Clinical Pharmacology 30 Suppl 1 125s–127s, 1990, Abstract.*
Acosta–Marinez, M., et al. (1999) "Localization of alpha$_{1B}$–adrenergic in female rat brain regions involved in stress and neuroendocrine function," *Neurochem. Intl.* 35:383–391.
Bakshi, V.P. and Geyer, M.A. (1999) "Alpha–1–Adrenergic Receptors Mediate Sensorimotor Gating Deficits Produced by Intracerebral Dizocilpine Administration in Rats," *Neurosci.* 91:113–121.
Carasso, B.S., et al. (1998) "Disruption in prepulse inhibition after alpha–1 adrenoceptor stimulation in rats," *Neuropharmacol.* 37:401–404.
Chang, D.J., et al. (1998) "Molecular cloning, genomic characterization and expression of novel human alpha$_{1A}$–adrenoceptor isoforms," *FEBS Letts.* 422:279–283.
Gogas, K.R., et al. (1997) "The Cold Bath Assay: A Simple and Reliable Method to Assess Cold Allodynia in Neuropathic Rats," *Analgesia* 3:111–118.
Janni, G. and Jasmin, L. (1998) "Persistence of Cold Hyperalgesia in Inflammatory and Neuropathic Pain Models as Determined with the Cold Plate," *Soc. Neurosci.* 24:882; Abstract No. 349.14.
Lee, D.H., et al. (1999) "Receptor Subtype Mediating the Adrenergic Sensitivity of Pain Behavior and Ectopic Discharges in Neuropathic Lewis Rats," *J. Neurophysiol.* 2226–2233.
Lee, D.H. and Chung, J.M. (1997) "Effects of Adrenergic Blockers on Neuropathic Pain in an Experimental Animal Model," *Soc Neurosci.* 23:1534; Abstract No. 599.19.
Lee, D.H., et al. (1997) "Strain differences in adrenergic sensitivity of neuropathic pain behaviors in an experimental rat model," *NeuroReport* 8:3453–3456.
Xie, J., et al. (1998) "Increase in alpha$_{1B}$Adrenergic Receptor mRNA Expression in the Rat Dorsal Root Ganglion (DRG) after Spinal Nerve Injury," *Soc. Neurosci.* 24:2089; Abstract No. 832.17.

* cited by examiner

*Primary Examiner*—Yvonne Eyler
*Assistant Examiner*—Michael Brannock
(74) *Attorney, Agent, or Firm*—Robert C. Hall; Rohan Peries

(57) ABSTRACT

A method for identifying compounds that can be useful for producing analgesia is disclosed. In particular, the method involves providing preparation of a cell, that expresses an alpha$_{1B}$ adrenergic receptor, combining a test compound with the cell preparation, measuring the effect of the test compound on the alpha$_{1B}$ receptor activity, and evaluating the compound thus identified for analgesic activity.

14 Claims, No Drawings

METHOD FOR SCREENING COMPOUNDS FOR ALPHA$_{1B}$ ADRENERGIC RECEPTOR ANTAGONIST AND ANALGESIC ACTIVITY

CROSS-REFERENCE TO RELATED APPLICATIONS

This application claims benefit under 35 U.S.C §119(e) of U.S. Provisional Application No. 60/124,721, filed Mar. 17, 1999; and makes reference to the commonly owned U.S. patent applications U.S. S.No. 60/124,781; filed on Mar. 17, 1999; U.S. S.No. 60/165,132 filed Nov. 12, 1999; and U.S. Ser. No. 09/521,185 filed Mar. 8, 2000 by Coffen et al. entitled "Oxazolone Derivatives and Uses Thereof", filed herewith.

FIELD OF THE INVENTION

The present invention relates generally to the discovery that selective alpha$_{1B}$ adrenergic receptor antagonists can be useful for the treatment of pain. In particular, the present invention relates to methods for screening compounds to identify an alpha$_{1B}$ adrenergic receptor ligand that binds to the alpha$_{1B}$ adrenergic receptor to provide an analgesic effect.

BACKGROUND

Alpha$_1$ adrenergic receptors are G-protein coupled transmembrane receptors that mediate various actions of the sympathetic nervous system through the binding of the catecholamines, epinephrine and norepinephrine. Currently, several subtypes of the alpha$_1$ adrenergic receptors are known to exist for which the genes have been cloned: alpha$_{1A}$ (previously known as alpha$_{1C}$), alpha$_{1B}$ and alpha$_{1D}$. The existence of an additional subtype, the alpha$_{1L}$ adrenergic receptor subtype, has been proposed; however, the gene for the alpha$_{1L}$ adrenergic receptor subtype has yet to be cloned. Although these subtypes can be pharmacologically distinguished, existing subtype-selective compounds are only moderately specific and may interact with more than one alpha$_1$ adrenergic receptor subtype. (See Giardina, D., et al., *J. Med. Chem.*, 1996, 39:4602–4607). Accordingly, therapeutic use of nonselective alpha$_1$ adrenergic receptor antagonists must be carefully monitored as such antagonists can produce significant undesirable side effects such as postural hypotension, sedation or depression, increased gastrointestinal motility and diarrhea, impaired ability to ejaculate, nasal stuffiness, akinesia and the like.

Compounds that interact more selectively with a particular alpha$_1$ adrenergic receptor subtype may prove clinically useful in providing more selective treatment of conditions and diseases associated with abnormal activity at the receptor subtype. For example, alpha$_1$ adrenergic receptor antagonists that can selectively ameliorate nociceptive and/or neurogenic pain without affecting blood pressure or causing postural hypotension, are desirable. Presently available alpha$_1$ adrenergic antagonists are either relatively nonselective with respect to the subtypes with which they interact or are not selective for the alpha$_{1B}$ adrenergic receptor subtype.

Selective alpha$_{1B}$ adrenergic receptor antagonists can also be useful in the treatment of CNS disorders including, but not limited to, anxiety, sleep disorders, and schizophrenia. (See, e.g., Bakshi et al. (1999) *Neuroscience* 92:113–121; Carasso, et al. (1998) *Neuropharmacol.* 37:401–404; and Acosta-Martinez, et al. (1999) *Neurochem. Int.* 35:383–391.)

The present invention relates to the discovery of a preferred class of novel compounds that are selective alpha$_{1B}$ adrenergic receptor antagonists (see, commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof," filed herewith, the disclosure of which are incorporated by reference herein), and that alpha$_{1B}$ adrenergic receptor-selective compounds possess analgesic activity.

SUMMARY OF THE INVENTION

Accordingly, there is a need in the art for a method by which compounds can be identified having alpha$_{1B}$ adrenergic receptor-mediated analgesic activity.

It is a primary object of the invention to addressed the above-described need in the art.

It is another object of the invention to provide a method by which compounds can be screened to identify those that produce alpha$_{1B}$ adrenergic receptor-mediated analgesia.

It is still another object of the invention to provide compounds identified by the aforementioned method.

It is yet another object of the invention to provide a method of treating a subject to produce analgesia comprising administering to the subject in need of analgesia a therapeutically effective amount of a compound identified by the aforementioned method, or a pharmaceutically acceptable salt or hydrate thereof, or pharmaceutical composition comprising such a compound, or salt or hydrate thereof.

In one embodiment of the invention, a method for screening for compounds having alpha$_{1B}$ adrenergic receptor-mediated analgesic activity is provided. The method comprises (a) measuring the activity of a test compound in a first binding assay and (b) measuring activity of the test compound in at least one pain model, wherein (a) and (b) are done concurrently or consecutively in any order. The first binding assay comprises (i) providing a preparation of a cell that expresses an alpha$_{1B}$ adrenergic receptor, (ii) combining a test compound with the cell preparation, and (iii) measuring binding of the test compound to the cell preparation or the receptor. The test compound is also be evaluated in a second binding assay for its ability to bind to the alpha$_{1A}$ and/or alpha$_{1D}$ adrenergic receptor, and/or to other receptors, e.g., histamine receptors, dopamine receptors, and the like. A test compound is also evaluated for its ability to elicit an appropriate response in at least one pain model, e.g., the ability to reduce nociceptive or neurogenic pain. Optionally, test compounds are evaluated for other alpha$_1$ adrenergic receptor-mediated functional activity.

The invention includes a method of treating a subject for the production of analgesia. The phrases "production of analgesia" and "reduction of pain" are used interchangeably herein. In the method, a therapeutically effective amount of a compound identified by the method disclosed and claimed herein, or a pharmaceutically acceptable salt or hydrate thereof, is administered to a subject in need of a reduction of pain. The compound can be administered after a trauma that causes acute or chronic pain. Optionally, the compound, or a pharmaceutically acceptable salt or hydrate thereof, can be administered as a composition comprising one or more pharmaceutically acceptable additives, diluents, or carriers to form a pharmaceutical composition. In one embodiment, such a composition is a sustained release formulation.

In a further embodiment, the pharmaceutical composition can also include one or more compounds having at least one of antiinflammatory activity, analgesic activity, and anticonvulsant activity. Examples of other compounds include, but are not limited to the following: compounds used in the treatment of neuropathic pain including, but not limited to tricyclic antidepressants (e.g., amitriptyline, imipramine, desipramine), anti-convulsants (e.g., gabapentin, carbamazepine, phenytoin) and local anesthetics (e.g., mexiletine, lidocaine); and compounds used in the treatment of inflammatory pain including, but not limited to nonsteroidal antiinflammatory agents, (e.g., ibuprofen, naprosyn sodium, aspirin, diclofenac sodium, indomethacin, toletin), steroids (e.g., methylprednisone, prednisone), analgesics (e.g., acetaminophen), and opiates (e.g., tramadol, demerol, darvon, vicodin, fentanyl).

Administration of a selected compound is accomplished by conventional means including but not limited to oral, enteral, rectal, mucosal, percutaneous, and parenteral administration. In a preferred embodiment, the selected compound is administered orally.

In another aspect, the invention includes a pharmaceutical composition, comprising (a) a therapeutically effective amount of a compound identified by the method disclosed and claimed herein, or a pharmaceutically acceptable salt or hydrate thereof, and (b) a pharmaceutically acceptable additive, diluent, or carrier. In one embodiment, this composition is a sustained release formulation.

In another embodiment, the present invention encompasses a method of treating a subject suffering from a CNS disorder comprising administering to the subject a therapeutically effective amount of a compound identified by the method of screening disclosed or a pharmaceutically acceptable salt or hydrate thereof. In a further embodiment, the subject suffering from a CNS disorder is administered a therapeutically effective amount of a composition comprising a compound identified by the method of screening disclosed or a pharmaceutically acceptable salt or hydrate thereof and a pharmaceutically acceptable carrier.

DETAILED DESCRIPTION OF THE INVENTION

The practice of the present invention will employ, unless otherwise indicated, conventional methods of chemistry, biochemistry, molecular biology, immunology and pharmacology, within the skill of the art. Such techniques are explained fully in the literature. See, e.g., *Remington: The Science and Practice of Pharmacy* 1995, edited by E. W. Martin, Mack Publishing Company, I9th edition, Easton, Pennsylvania; *Methods In Enzymology* (S. Colowick and N. Kaplan, eds., Academic Press, Inc.); *Textbook of Pain* (P. D. Wall and R. Meizack, editors, Third Edition, Churchill Livingstone, 1994); and Winzor et al. (1995) *Quantitative Characterization of Ligand Binding* (Wiley-Liss, Inc., NY).

All publications, patents and patent applications cited herein, whether supra or infra, are hereby incorporated by reference in their entirety.

As used in this specification and the appended claims, the singular forms "a," "an" and "the" include singular and plural references unless the content clearly dictates otherwise. Thus, for example, reference to "an antagonist" may include a mixture of two or more such agents.

I. Definitions

In describing the present invention, the following terms will be employed, and are intended to be defined as indicated below.

A "pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use as well as human pharmaceutical use. A "pharmaceutically acceptable carrier" as used in the specification and claims includes both one and more than one such carrier.

A "pharmaceutically acceptable salt" of a compound means a salt that is pharmaceutically acceptable, as described above, and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, benzenesulfonic acid, benzoic acid, 3-(4-hydroxybenzoyl)benzoic acid, camphorsulfonic acid, p-chlorobenzenesulfonic acid, cinnamic acid, citric acid, cyclopentanepropionic acid, ethanesulfonic acid, 1,2-ethanedisulfonic acid, fumaric acid, glucoheptonic acid, gluconic acid, glutamic acid, glycolic acid, hexanoic acid, heptanoic acid, (o-hydroxybenzoyl) benzoic acid, hydroxynaphthoic acid, 2-hydroxyethanesulfonic acid, lactic acid, lauryl sulfuric acid, malic acid, maleic acid, malonic acid, mandelic acid, methanesulfonic acid, 4-methylbicyclo[2.2.2]oct-2-ene-1-carboxylic acid, 4,4'-methylenebis(3-hydroxy-2-ene-1-carboxylic acid), muconic acid, 2-napthalenesulfonic acid, oxalic acid, 3-phenylpropionic acid, propionic acid, pyruvic acid, salicylic acid, stearic acid, succinic acid, tartaric acid, trimethylacetic acid, tertiary butylacetic acid, p-toluenesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. The preferred pharmaceutically acceptable salts are the salts formed from hydrochloric acid, sulphuric acid, methanesulfonic acid, maleic acid, phosphoric acid, tartaric acid, citric acid, sodium, potassium, calcium, zinc, and magnesium.

Pharmaceutically acceptable salts also include base addition salts which may be formed when acidic protons present are capable of reacting with inorganic or organic bases. Acceptable inorganic bases include aluminum hydroxide, calcium hydroxide, potassium hydroxide, sodium carbonate, and sodium hydroxide. Acceptable organic bases include diethanolamine, ethanolamine, N-methyl-glucamine, triethanolamine, tromethamine, and the like.

"Pharmaceutically acceptable hydrates" means hydrates, which are pharmaceutically acceptable, as defined above, and which possess the desired pharmacological activity. Such hydrates are formed by the combination of one or more molecules of water with one of the substances, in which the water retains its molecular state as $H_2O$, such combination being able to form one or more than one hydrate.

A "therapeutically effective amount" means an amount of a compound that, when administered to a subject for treating a disease, is sufficient to effect such treatment for the disease. The "therapeutically effective amount" will vary depending on the compound, and disease state being treated, the severity of the disease treated, the age and relative health of the subject, the route and form of administration, the judgement of the attending medical or veterinary practitioner, and other factors.

"$alpha_1$ adrenergic receptors", "$alpha_{1A}$ adrenergic receptors" (previously known as "$alpha_{1C}$ adrenergic receptors"), "$alpha_{1B}$ adrenergic receptors," "$alpha_{1D}$ adrenergic receptors", or "$alpha_{1L}$ adrenergic receptors" used interchangeably with "$alpha_1$ adrenoceptors", "$alpha_{1A}$ adrenoceptors" ("$alpha_{1C}$ adrenoceptors"), "$alpha_{1B}$ adrenoceptors", "alpha$_{1D}$ adrenoceptors", and "alpha$_{1L}$ adrenoceptors", respectively, refers to a molecule conforming to the seven membrane-spanning G-protein receptors, which under physiologic conditions mediate various actions, for example, of the central and/or peripheral sympathetic nervous system through the binding of the catecholamines, epinephrine and norepinephrine. Examples of physiological effects mediated by alpha$_1$ adrenoceptors include, but are not limited to, control of blood pressure, glycogenolysis, growth and hypertrophy of cardiac myocytes, contractility of the urinary tract, and the like.

The term "alpha$_1$ adrenergic receptor subtype" used interchangeably with "alpha$_1$ adrenoceptor subtype" refers to a distinct member of the class of alpha$_1$ adrenoceptors, selected from the alpha$_{1A}$ (previously known as alpha$_{1C}$), alpha$_{1B}$, alpha$_{1D}$ and alpha$_{1L}$ adrenoceptors. The subtypes have been distinguished based on differential binding profiles of ligands, such as the agonist oxymetazoline, and such as the antagonists, WB4101 and phentolamine. Furthermore, the genes encoding the alpha$_{1A}$ (previously known as alpha$_{1C}$), alpha$_{1B}$ and alpha$_{1D}$ subtypes have been isolated and cloned. The existence of an additional subtype, the alpha$_{1L}$ adrenergic receptor subtype, has been proposed, however, the gene for the alpha$_{1L}$ adrenergic receptor subtype has not yet been cloned.

The term "specific alpha$_1$ adrenergic receptor" as used herein, refers to a distinct member of the group or class of adrenoceptors, which may be selected from the human alpha$_{1A}$ (previously known as alpha$_{1C}$), alpha$_{1B}$, alpha$_{1D}$ and alpha$_{1L}$ adrenoceptors. Preferred species from which may be derived or isolated alpha$_1$ adrenergic receptor subtype polypeptides, genes encoding an alpha$_1$ adrenergic receptor subtype, and/or cells, tissues and organs that express one or more alpha$_1$ adrenergic receptor subtype, include human, bovine, rat, murine, porcine, ovine, and the like. A more preferred species is human.

"Alpha$_{1B}$ adrenergic receptors" means a specific alpha$_1$ adrenoceptor expressed in numerous tissues, most notably in the liver, heart, cerebral cortex, and spinal cord.

The term "cell preparation" as used herein with respect to the expression of an alpha$_1$ adrenergic receptor or an alpha$_1$ adrenergic receptor subtype intends any form of a cell that expresses the receptor or receptor subtype of interest in which receptor- or receptor subtype-specific binding of a ligand, a radioligand, a test compound, or the like, can be measured. The term "cell preparation" includes, but is not limited to, a tissue explant, an intact cell isolated from a subject or tissue, an intact cultured or recombinant cell, as well as a disrupted cell, e.g., a cell membrane homogenate, a solubilized cell membrane in which receptor-specific binding can be measured, and the like.

The term "pharmacological effect" as used herein encompasses effects produced in the subject that achieve the intended purpose of a therapy. In preferred embodiments, a pharmacological effect means that pain symptoms of the subject being treated are prevented, alleviated, or reduced. For example, a pharmacological effect would be one that results in the production of analgesia in a treated subject.

"Treating" or "treatment" of a disease includes: (1) preventing the disease, i.e. causing the clinical symptoms of the disease not to develop in a subject that may be exposed to or predisposed to the disease but does not yet experience or display symptoms of the disease, (2) inhibiting the disease, i.e., arresting the development of the disease or its clinical symptoms, or (3) relieving the disease, i.e., causing regression of the disease or its clinical symptoms.

The term "subject" as used herein encompasses mammals and non-mammals. Examples of mammals include, but are not limited to: any member of the Mammalia class, including humans, nonhuman primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs, and the like. Examples of nonmammals include, but are not limited to, birds, reptiles, and the like. The term does not denote a particular age or sex.

"Trauma" means any wound or injury. Trauma can produce, for example, acute and/or chronic pain, inflammatory pain, and neuropathic pain.

"Pain" means more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28th Edition, W. B. Saunders Company, Philadelphia, Pa.). The goal of treatment of pain is to reduce the degree or severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Hyperalgesia" means the abnormally increased pain sense, such as pain that results from an excessive sensitiveness or sensitivity.

"Hypalgesia" (or "hypoalgesia") means the decreased pain sense.

"Allodynia" means the pain that results from a nonnoxious stimulus to the skin. Examples of allodynia include, but are not limited to, cold allodynia, tactile allodynia, and the like.

"Complex regional pain syndromes" means the pain that includes, but is not limited to, reflex sympathetic dystrophy, causalgia, sympathetically maintained pain, and the like.

"Causalgia" means the burning pain, often accompanied by trophic skin changes, due to injury of a peripheral nerve.

"Nociception" is defined herein as pain sense. "Nociceptor" herein refers to a structure that mediates nociception. The nociception may be the result of a physical stimulus, such as, mechanical, electrical, thermal, or a chemical stimulus. Most nociceptors are in either the skin or the viscera walls.

"Analgesia" is defined herein as the relief of pain without the loss of consciousness. An "analgesic" is an agent or drug useful for relieving pain, again, without the loss of consciousness.

"Isomerism" means the compounds have identical molecular formulae but that differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes optical isomers. A carbon atom bonded to four nonidentical substituents is termed a "chiral center."

"Chiral isomer" means a compound with one chiral center. It has two enantiomeric forms of opposite chirality, and may exist as either an individual enantiomer or as a mixture of enantiomers. A mixture containing equal amounts of individual enantiomeric forms of opposite chirality is termed a "racemic mixture." A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture."

When one chiral center is present a stereoisomer may be characterized by the absolute configuration (R) or (S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia* 1956, 12, 81; Cahn, *J. Chem. Educ.* 1964, 41, 116).

"Geometric isomers" means the diastereomers that owe their existence to hindered rotation about double bonds. Their configurations are differentiated in their names by prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

Reference to a "compound" includes individual isomers as well as racemic or nonracemic mixtures of isomers, and pharmaceutically acceptable salts or hydrates thereof.

"Optional" or "optionally" means that the subsequently described event or circumstance may or may not occur, and that the description includes instances where the event or circumstance occurs and instances in which it does not. For example, the phrase "optionally, test compounds are evaluated for other $alpha_1$ adrenergic receptor-mediated functional activity" means that the compound referred to may or may not be evaluated as described in order to fall within the scope of the invention, and that the description includes the situation wherein the compound is evaluated and the situation in which the compound is not evaluated for other $alpha_1$ adrenergic receptor mediated functional activity.

The Invention

Before describing the present invention in detail, it is to be understood that this invention is not limited to particular formulations, process parameters, or the order in which method steps are performed as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

A. Pharmacology and Utility

The present invention is based on the unexpected finding that selective $alpha_{1B}$ adrenergic receptor antagonists have specific analgesic activity.

1. Selective $Alpha_{1B}$ Adrenergic Receptor Binding Activity

The receptor specificity of a test compound can be determined by any method well known in the art. In one preferred embodiment, the binding of compounds at different receptors, including but not limited to, human, bovine, rat, murine, porcine, ovine, and the like, receptors, preferably human receptors, can be determined in vitro using cultured cell lines that selectively express the receptor of interest.

Cell Lines That Express Receptors of Interest

Examples of cell lines that are available from the American Type Culture Collection (ATCC) that express human receptors as follows (ATCC Accession No.): $alpha_{1A}$ (CRL 11138), $alpha_{1B}$ (CRL 11139), $alpha_{1C}$ (CRL 11140), $alpha_{2A}$ (CRL 11180), $alpha_{2B}$ (CRL 10275, CRL 11888), $alpha_{2C}$ (CRL 11181), $5\text{-HT}_{1D1}$ (CRL 10421), $5\text{-HT}_{1D2}$ (CRL 10422), $5\text{-HT}_{1E}$ (CRL 10913), $5\text{-HT}_{1F}$ (CRL 10957), $5\text{-HT}_{4B}$ (CRL 11166), $5\text{-HT}_{1A}$ (CRL 11889) and $5\text{-HT}_2$ (CRL 10287).

In addition, plasmids are available from the ATCC that harbor cloned human D2, H2 and H1 receptors (ATCC Accession Nos. 7534, 75345 and 75346, respectively) that can be used to transfect cells using conventional methods well known in the art to provide cells that express on their surface the receptor of interest. Transient transfection of COS-7 cells with a plasmid can be performed using any method known in the art, e.g., the DEAE-dextran method. Briefly, a plasmid comprising an expression vector for the receptor of intrest is added to monolayers of COS-7 cells bathed in DEAE-dextran solution. To enhance the efficiency of transfection diemthyl sulfoxide can be added (Lopata et al. (1984) *Nucleic Acids Res.* 12:5707–5717). Cells are then grown under controlled conditions and used in experiments after about 72 hours. Stable cells lines can also be obtained by methods well known in the art. For example, a suitable host cell can be cotransfected using, e.g., the calcium phosphate method, with a plasmid comprising an expression vector for the receptor of interest and a plasmid comprising a gene that allows for selection of successfully tranfected cells. Cells are then grown in a controlled environment and selected for expression of the receptor of interest. By continuing to grow and select cells stable, cell lines can be obtained expressing the receptor of interest.

Additional reference with respect to the preparation of DNA encoding these receptors and recombinant cells expressing the DNA can be made to U.S. Pat. No. 5,610,174 to Craig et al., U.S. Pat. Nos. 5,556,753 and 5,714,381 to Bard et al., U.S. Pat. Nos. 5,155,218, 5,360,735, 5,476,782, 5,595,880, 5,639,652, 5,652,113, 5,786,155 and 5,786,157 to Weinshank et al., and U.S. Pat. Nos. 5,403,847, 5,578,611, and 5,780,485 to Gluchowski et al.

Binding Assays

The binding of a test compound to a receptor of interest can be detected by use of a radioligand selective for the receptor. Any radioligand binding technique known in the art may be used to detect the receptor (see, e.g., Winzor et al. (1995) *Quantitative Characterization of Ligand Binding*, Wiley-Liss, Inc., NY). Binding assays, the evaluation of analgesic activity of a test compound, and/or the evaluation of other functional $alpha_1$ adrenergic receptor-mediated activity of a test compound, as described hereinbelow, can be carried out concurrently and/or consecutively, in any order.

The binding of a test compound to a receptor of interest can be evaluated by, e.g., competitive binding assays using membrane preparations derived from cells that express the receptor or, alternatively, intact cells that express the receptor can be used. First, conditions are determined that allow measurement of the specific binding of a compound known to bind to the receptor. Then, the binding of the known compound to the receptor in a membrane preparation or intact cell preparation is evaluated in the presence of several different concentrations of the test compound. Binding of the test compound to the receptor results in a diminution in the amount of the known compound that binds to the receptor. A test compound having a high affinity for the receptor of interest displaces a given fraction of the bound known compound at a concentration lower than the concentration that would be required if the test compound has a low affinity for the receptor of interest. Thus, for example, competitive radioligand binding assays can be done using the following radioligand/compound combinations for determining specific and nonspecific binding for receptors of interest: [$^3$H]prazosin/phentolamine (alpha$_1$); [$^3$H]rauwolscine/phentolamine (alpha$_2$); [$^3$H]mepyramine/mepyramine (H$_1$); [$^3$H]tiotidine/histamine (H$_2$); [$^3$H]serotonin/serotonin (5-HT$_1$); [$^3$H]ketanserin/mianserin (5-HT$_2$);[$^3$H]-8-OH-DPAT/mianserin (5-H$_1$A); and [$^3$H]spiperone/(+)butaclomol (D$_2$).

2. Pain Models

The analgesic activity of a test compound can be evaluated by any method known in the art. Such methods are described in detail in Examples 1 through 12, below. The evaluation of analgesic activity of a test compound, and/or the evaluation of other functional alpha$_1$ adrenergic receptor-mediated activity of a test compound, as described hereinbelow, and the binding activity of a test compound, as described above, can be carried out concurrently and/or consecutively, in any order.

3. Motor Activity

The effects of alpha$_{1B}$ adrenergic receptor antagonists on general locomotor activity and sedation can be examined. Locomotor deficits or sedation are both common side effects of potential analgesic compounds. The locomotor activity test is described in Example 13, below.

4. Functional Activity

The functional alpha$_1$-adrenergic receptor activity of a test compound can be determined by art-recognized procedures. Such studies are conducted to determine whether a test compound exhibits agonist or antagonist activity at alpha$_1$ adrenergic receptor. Such activity can be indicative of potential side effects. Examples of in vitro and in vivo assays for measuring the relative effect of a test compound on alpha$_1$ adrenergic receptor-mediated activity, either agonist or antagonist activity, are described in Examples 14 through 18, below.

5. Neuropsychiatric Disorders

The assay of the present invention can be employed to screen for compounds useful in the treatment of neuropsychiatric disorders. These disorders include, but are not limited to, generalized anxiety, sleep disorders, and schizophrenia. Animal models are also available to concurrently or subsequently test potential therapeutics found by the assay of the present invention. These animal models are well known in the art and are described, e.g., in Bakshi, et al. (1999) supra; Carasso, et al. (1998) supra; and Acosta-Martinez, et al. (1999) supra.

B. Administration and Pharmaceutical Compositions

A compound identified as a selective alpha$_{1B}$ adrenergic receptor antagonist by the method disclosed and claimed herein, when employed in the prevention or treatment of pain or neuropsychiatric disorders, can be formulated neat or with the addition of pharmaceutically acceptable excipients, additives, diluents, or carriers (see, for example, formulations as described in *Remington: The Science and Practice of Pharmacy,* supra.

The invention includes a pharmaceutical composition comprising at least one compound identified as a selective alpha$_{1B}$ adrenergic receptor antagonist by the method disclosed and claimed herein or a pharmaceutically acceptable salt, hydrate, or derivative thereof together with one or more pharmaceutically acceptable carriers, and optionally other therapeutic and/or prophylactic ingredients.

In general, a compound identified as a selective alpha$_{1B}$ adrenergic receptor antagonist by the method disclosed and claimed herein will be administered in a therapeutically effective amount by any of the accepted modes of administration for agents that serve similar utilities. Suitable dosage ranges are about 1–500 mg daily, preferably about 1–100 mg daily, and more preferably about 1–30 mg daily, depending upon numerous factors such as the severity of the disease to be treated, the age and relative health of the subject, the potency of the compound used, the route and form of administration, the indication towards which the administration is directed, and the preferences and experience of the medical or veterinary practitioner involved. One of ordinary skill in the art of treating such diseases will be able, without undue experimentation and in reliance upon personal knowledge and the disclosure of this application, to ascertain a therapeutically effective amount of the compounds of this invention for a given disease.

In general, a compound identified as a selective alpha$_{1B}$ adrenergic receptor antagonist by the method disclosed and claimed herein will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is oral using a convenient daily dosage regimen which can be adjusted according to the degree of affliction.

A compound identified as a selective alpha$_{1B}$ adrenergic receptor antagonist by the method disclosed and claimed herein, together with a conventional adjuvant, carrier, or diluent, may be placed into the form of pharmaceutical compositions and unit dosages. The pharmaceutical compositions and unit dosage forms may comprise of conventional ingredients in conventional proportions, with or without additional active compounds or principles, and the unit dosage forms may contain any suitable effective amount of the active ingredient commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about 0.01 to 100 milligrams, preferably about 1 to 50 milligrams, more preferably about 1 to 10 milligrams, per tablet, are accordingly suitable representative unit dosage forms.

A compound identified as a selective alpha$_{1B}$ adrenergic receptor antagonist by the method disclosed and claimed herein may be formulated in a wide variety of oral administration dosage forms. The pharmaceutical compositions and dosage forms may comprise the compound or its pharmaceutically acceptable salt or hydrate as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

A compound identified as a selective $alpha_{1B}$ adrenergic receptor antagonist by the method disclosed and claimed herein may be formulated for parenteral administration (e.g., by injection, for example bolus injection or continuous infusion) and may be presented in unit dose form in ampules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

A compound identified as a selective $alpha_{1B}$ adrenergic receptor antagonist by the method disclosed and claimed herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

A compound identified as a selective $alpha_{1B}$ adrenergic receptor antagonist by the method disclosed and claimed herein may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

A compound identified as a selective $alpha_{1B}$ adrenergic receptor antagonist by the method disclosed and claimed herein may be formulated for vaginal administration. Pessaries, tampons, creams, gels, pastes, foams or sprays containing in addition to the active ingredient such carriers as are known in the art to be appropriate.

A compound identified as a selective $alpha_{1B}$ adrenergic receptor antagonist by the method disclosed and claimed herein may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

A compound identified as a selective $alpha_{1B}$ adrenergic receptor antagonist by the method disclosed and claimed herein may be formulated for aerosol administration, particularly to the respiratory tract and including intranasal administration. The compound will generally have a small particle size for example of the order of about 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoro-ethane, carbon dioxide or other suitable gas. The aerosol may conveniently also contain a surfactant such as lecithin. The dose of compound may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy,* supra. Representative pharmaceutical formulations containing a compound of the present invention are described in Example 19.

In addition to being administered alone, an $alpha_{1B}$ adrenergic receptor antagonist can be administered for the treatment of pain in combination with other appropriate compounds, such as, analgesics or anticonvulsants. Such compounds include, but are not limited to the following: agents used in the treatment of neuropathic pain including, but not limited to, tricyclic antidepressants (e.g., amitriptyline, imipramine, desipramine), anticonvulsants (e.g., gabapentin, carbamazepine, phenytoin) and local anesthetics (e.g., mexiletine, lidocaine); and agents used in the treatment of inflammatory pain including, but not limited to, NSAIDs (e.g., ibuprofen, naprosyn sodium, aspirin, diclofenac sodium, indomethacin, toletin), steroids (e.g., methylprednisone, prednisone), analgesics (e.g., acetaminophen), and opiates (e.g., tramadol, demerol, darvon, vicodin, fentanyl).

In view of the guidance provided herein concerning the present invention, other compounds, including other alpha adrenergic receptor ligands, that block $alpha_{1B}$ adrenergic receptors can be examined by the teachings of the present specification to determine their usefulness in the treatment of pain. Determination of a compound's ability to selectively block $alpha_{1B}$ adrenergic receptors can be performed as described in Example 1. The usefulness of the compound for the treatment of pain can be evaluated as described herein in Examples 2–6. Binding assays, the evaluation of analgesic activity of a test compound, and/or the evaluation of other functional $alpha_1$ adrenergic receptor-mediated activity of a test compound, as described herein, can be carried out concurrently and/or consecutively, in any order, and near or remote in time.

As stated above, the role of $alpha_{1B}$ adrenergic receptor antagonists in analgesia has not been previously described. Experiments performed in support of the present invention suggest that $alpha_{1B}$ adrenergic receptor antagonists may be useful in the treatment of acute, inflammatory, and neuropathic pain in a subject. Furthermore, compounds identified through the assay of the present invention are useful in the treatment of neuropsychiatric disorders.

Below are examples of specific embodiments of the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLES

Example 1
Screening Compounds for Selective $alpha_{1B}$ Adrenergic Receptor Antagonist Activity: In Vitro Selection Using Recombinant Receptors $Alpha_{1A}$, $alpha_{1B}$ and $Alpha_{1D}$ adrenergic receptor transfected CHO-K1 cells, prepared using the methods described in Chang et al. (1998) *FEBS Lett.* 422:279–283, were grown to confluence in T-162 tissue culture flasks in Ham's F-12 culture medium supplemented with 10% fetal bovine serum, geneticin (150 µg/ml) and streptomycin: penicillin (30 µg/ml:30 µg/ml) at 37° C. in 7% $CO_2$. Cells were harvested by incubating with phosphate-buffered saline (PBS) containing 30 µM EDTA for 5–10 min at 37° C. Cells were pelleted by centrifuging at 500×g for 5 min, the pelleted cells were homogenized (Polytron homogenizer) in 10 vols (w/v) of 50 mM Tris, 1 mM EDTA, (homogenisation buffer, pH 7.4 at 4° C.). The homogenate was centrifuged at 45,000×g for 20 min. The pellet was resuspended in the homogenizing buffer and rehomogenized. The rehomogenate was centrifuged at 45,000×g for 20 min. The pellet was resuspended in 50 mM Tris buffer (pH 7.4 at 4° C.), aliquoted, frozen, and stored at −80° C. for further use.

The membranes were thawed at room temperature and diluted in assay buffer (50 mM Tris, pH 7.4) at 37° C. and homogenized using the Polytron tissue disrupter. The membranes were incubated with the radioligand ([$^3$H]prazosin, NEN, 0.1–0.5 nM) and test compound at 37° C. for 30 min. The membranes were then filtered over polyethyleneimine-treated GF/B unifilter plates using a Packard Filtermate Harvester and washed with ice-cold 50 mM Tris-HCl, 1 mM EDTA buffer (3×3-sec. washes). Scintillation cocktail was added to the filter plates and bound radioligand determined by liquid scintillation spectrophotometry.

For each experiment, total binding (in the absence of any test or reference compounds) and non specific binding (10 µM phentolamine) were determined. For each sample tested, the concentration producing 50% inhibition of binding ($IC_{50}$) and Hill Slope ($n_H$) was determined using iterative non-linear curve fitting techniques with Kaleidagraph (Synergy Software) or other appropriate software. If the radioligand $K_D$ was known, the inhibition dissociation constant ($K_i$) of each ligand was determined according to the method of Cheng et al. (1973) *Biochem. Pharmacol.* 22:3099–3108).

In preferred embodiments, the compounds disclosed commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof," filed herewith, were evaluated using this method and found to have $alpha_{1B}$ adrenergic receptor binding activity.

Alternatively, cells naturally expressing $alpha_{1A}$, $alpha_{1B}$ and $alpha_{1D}$ receptors are utilized with the methods described above.

Example 2
Effect of the $alpha_{1B}$ Adrenerigic Receptor Antagonist on the Pain Response to Radiant Heat in Neuropathic Rats This experiment was conducted to evaluate the effects of 4-(2-benzofuran-7-yl-5-oxo-oxazol-4-ylidenemethyl)-N-phenyl-piperazine-1-carboxamidine hydrochloride and similar or related compounds on the pain response to radiant heat in neurpathic rats.

4-(2-Benzofuran-7-yl-5-oxo-oxazol-4-ylidenemethyl)-N-phenyl-piperazine-1-carboxamidine hydrochloride was prepared as described in commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof," filed herewith. Briefly, methyl iodide (301 g, 2.12 mol) was added dropwise, over 30 min, to a solution of phenyl thiourea (300 g, 1.93 mol) in ethanol (1.5 L). The resulting solution was refluxed for 1 hour and cooled to room temperature. Concentration of the solution to approximately half its volume yielded a white precipitate that was collected by filtration, washed on the filter with diethyl ether and dried to yield a white solid (532 g). The white solid (200 g, 0.68 mol) was dissolved in 4M aqueous sodium hydroxide (1 L) and the resulting solution extracted with chloroform (4×400 mL). The combined chloroform extracts were dried over anahydrous magnesium sulfate, filtered and evaporated under reduced pressure yielding a thick oil (92.7 g).

N-tert-butoxycarbonyl-piperazine (100 g, 0.54 mol) was added to a solution of thick oil (89.1 g, 0.54 mol) in isopropanol (1 L), and the mixture refluxed overnight. The mixture was cooled to room temperature and the volatile materials removed under reduced pressure. Recrystallization of the residue from ethano/H$_2$O yielded a white solid (82.0 g).

A solution of the white solid (25.7 g) in dichloromethane (125 mL) was cooled to 0° C. and trifluoroacetic acid (125 mL) added dropwise over 30 min. The ice bath was removed and the mixture was warmed up to room temperature and stirred for 1 h. Removal of the volatile materials under reduced pressure followed by recrystallization from ethanol/diethyl ether yielded the desired product as its trifluoroacetate salt. $^1$H NMR: (DMSO d6) □9.08 (br. s, 1H, exch. D$_2$O), 8.22 (br. s, 1H, exch. D$_2$O), 7.53 (m, 2H), 7.34 (m, 3H), 3.78 (m, 4H), 3.36 (m, 4H).

To a suspension of 4-(2-benzofuran-7-yl-5-oxo-oxazol-4-ylidenemethyl)-N-phenyl-piperazine-1-carboxamidine trifluoroacetate (672 mg, 1.55 mmol) and 2-benzofuran-7-yl-4-ethoxymethylene-4H-oxazol-5-one (400 mg, 1.55 mmol) in acetonitrile (15 mL) was added N,N-diisopropylethylamine (1.0 g, 7.77 mmol) and the mixture stirred at room temperature for 1 h. The volatile materials were removed under reduced pressure and the residue recrystallized from ethanol/diethyl ether saturated with gaseous HCl to yield the desired product as its hydrochloride salt (202 mg). M$^+$415, $^1$H NMR: (DMSO d6) delta 8.17 (br. s, 1H, exch. D$_2$O), 8.11 (m, 1H), 7.82 (m, 2H), 7.53 (s,1H), 7.48–7.36 (m, 3H), 7.29–7.23 (m, 3H), 7.09 (m, 1H), 4.57 (m, 2H), 3.87 (m, 2H), 3.77 (m, 4H).

In preferred embodiments, compounds described in U.S. patent application U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof", filed herewith, including 4-(2-benzofuran-7-yl-5-oxo-oxoazol-4-ylidenemethyl)-N-phenyl-piperazine-1-carboxamidine hydrochloride, have been identified as selective alpha$_{1B}$ adrenergic receptor antagonists using the methods described in Example 1.

Male Sprague-Dawley rats (Harlan), 240–300 g, were surgically prepared to have a chronic constriction injury (CCI) as described above 13–15 days prior to testing. Rats were selected for the study according to the following criteria: ligated leg (L$_L$)latency–4 to 14 seconds; sham leg (L$_S$) latency–6 to 18 seconds; difference (L$_{Diff}$=L$_L$-L$_S$)–greater than 1.5 seconds. Selected rats were randomly assigned to treatment groups and dosed at 0 (vehicle, 10 ml/kg, 0.5% CMC, 30, 60, 100 or 300 µg/kg, i.p. After 45 minutes post-dosing, rats were placed under inverted plastic cages on an elevated glass platform. Following 15 minutes of acclimatization, a radiant heat source, e.g., light was placed below the glass and illuminated in order for the glass to reach a temperature of 80–82° F. For each rat, four trials of each of the following were performed: shone light on the left hind paw (sham) and recorded the latency when the paw was withdrawn; shone light on the right hind paw (ligated) and recorded the latency when the paw was withdrawn. Five minute intervals were allowed between trials. Hind paws were examined for redness and blistering after each test.

The results from these experiments indicate that 4-(2-benzofuran-7-yl-5-oxo-oxazol-4-ylidenemethyl)-N-phenyl-piperazine-1-carboxamidine hydrochloride had a significant effect in the radiant heat assay at the 60, 100 and 300 µg/kg doses.

In preferred embodiments, other compounds, including those described in commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof", filed herewith, can also be tested using the aformentioned assay.

Example 3

Effect of an alpha$_{1B}$ Adrenergic Receptor Antagonist on the Cold Allodynia Response in Neuropathic Rats This experiment was conducted to evaluate the effects of 4-(2-benzofuran-7-yl-5-oxo-oxazol-4-ylidenemethyl)-N-phenyl-piperazine-1-carboxamidine hydrochloride, and similar or related compounds, on the cold allodynia response in neuropathic rats. The test apparatus and methods of behavioral testing is described in Gogas et al. (1997) *Analgesia* 3:111–118.

Male Sprague-Dawley rats (Harlan), 160–200 g, were surgically prepared to have a chronic constriction injury (CCI) as described above 6 days prior to testing. Rats were selected for the study according to the following criteria: 1) the average of two trials was less than or equal to 13 sec; and 2) there was consistency across the two trial scores. Animals were screened for hypersensitivy to cold on post-surgery days 4 through 10, and selected for inclusion in dose-response studies based on the criteria described above. The pre-dose screening values were used as the animals' baseline cold allodynia scores.

Selected rats were tested twice in the cold bath assay described above for a pre-dose baseline and randomly assigned to treatment groups and dosed at 0 (vehicle, 10 ml/kg, 0.5% CMC, 30, 100 or 300 µg/kg, i.p. After 1 hour and 3 hours post-dosing, rats were tested in the cold bath assay. For each rat, the assay was run once at 1 and 3 hours post-dose. The time to raise the rear leg was recorded in each trial. The maximal observing time in each trial was 20 seconds.

The results from these experiments indicate that, at 1 hour post-dose, 4-(2-benzofuran-7-yl-5-oxo-oxazol-4-ylidenemethyl)-N-phenyl-piperazine-1-carboxamidine hydrochloride at the doses of 100 and 300 µg/kg both were significantly higher than vehicle as to the changes from pre-dose (both p<0.01). At 3 hours post-dose the compound at 300 µg/kg was significantly higher than vehicle as to the changes from pre-dose (p<0.05).

The results of analyses for group comparisons indicate that at 1 hour post-dose 4-(2-benzofuran-7-yl-5-oxo-oxazol-4-ylidenemethyl)-N-phenyl-piperazine-1-carboxamidine hydrochloride at 100 and 300 µg/kg both were significantly higher than vehicle as to the actual latency times (both p<0.01). At 3 hours post-dose, the compound at 300 µg/kg was significantly higher than vehicle as to the actual latency times (p<0.05).

In preferred embodiments, other compounds, including those described in commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen et al. entitled "Oxazolone Derivatives and Uses Thereof", filed herewith, can also be tested using the aformentioned assay.

Example 4

Effect of the alpha$_{1B}$ Adrenergic Receptor Antagonist on the Pain Response to Radiant Heat in Neuropathic Rats This experiment was conducted to evaluate the effects of 4-(2-naphthalen-1-yl-5-oxo-oxazol-4-ylidenemethyl)-N-phenyl-piperazine-1-carboxamidine, and similar or related compounds, on the pain response to radiant heat in neuropathic rats.

4-(2-Naphthalen-1-yl-5-oxo-oxazol-4-ylidenemethyl)-N-phenyl-piperazine-1-carboxamidine was prepared as described in commonly owned U.S. patent applications U.S.

S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof", filed herewith. Briefly, to a 0.25 M solution of N-phenyl-piperazine-1-carboxamidine (200 μL, 50 μmole) was added a 0.25 M solution of 4-ethoxymethylene-2-naphthalene-1-yl-4H-oxazol-5-one in DMSO (200 μL, 25 μmole). The reaction vessel was sealed and the resulting mixture shaken at room temperature for 1 h to yield the desired product as a DMSO solution (MH$^+$426).

This compound has been identified as a selective alpha$_{1B}$ adrenergic receptor antagonist using the methods described in Example 1.

Male Sprague-Dawley rats (Harlan), 240–300 g, were surgically prepared to have a CCl as described above 19–21 days prior to testing. Rats were selected for the study according to the following described in Example 2. Selected rats were randomly assigned to treatment groups and dosed with 4-(2-naphthalen-1-yl-5-oxo-oxazol-4-ylidenemethyl)-N-phenyl-piperazine-1-carboxamidine at 0 (vehicle, 10 mL/kg deionized water, 30, 60, 100, 300 or 1000 μg/kg, i.p. After 1 hour post-dosing, rats were tested as described in Example 2.

The results from these experiments indicate that 4-(2-naphthalen-1-yl-5-oxo-oxazol-4-ylidenemethyl)-N-phenyl-piperazine-1-carboxamidine had a significant effect in the radiant heat assay at the 60, 100, 300 and 1000 μg/kg doses.

In preferred embodiments, other compounds, including those described in commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof," filed herewith, can also be tested using the aforementioned assay.

Example 5
Effect of an alpha$_{1B}$ Adrenergic Receptor Antagonist on the Cold Allodynia Response in Neuropathic Rats This experiment was conducted as described in Example 3 to evaluate the effects of 4-(2-naphthalen-1-yl-5-oxo-oxazol-4-ylidenemethyl)-N-phenyl-piperazine-1-carboxamidine, and similar or related compounds, on the cold allodynia response in neuropathic rats.

Male Sprague-Dawley rats (Harlan), 160–270 g, were surgically prepared to have a chronic constriction injury (CCl) as described above 5 days prior to testing. Rats were selected and tested as described in Example 3. Selected rats were dosed at 0 (vehicle, 10 mL/kg, deionized water), 30 or 300 μg/kg, i.p. After 20 min and 40 minutes post-dosing, rats were tested in the cold bath assay.

These results indicate that 4-(2-naphthalen-1-yl-5-oxo-oxazol-4-ylidenemethyl)-N-phenyl-piperazine-1-carboxamidine at 20 min post-dose exhibited a significant increase in latency from pre-dose when compared to the vehicle group at the both 30 and 300 μg/kg. At 40 min post-dose only the group receiving 300 μg/kg had a significant change from pre-dose when compared to vehicle at the same time point.

4-(2-Naphthalen-1-yl-5-oxo-oxazol-4-ylidenemethyl)-N-phenyl-piperazine-1-carboxamidine showed a significant change in latency times when compared to pre-dose at 20 min post-dose. At 40 min post-dose, only the group receiving 300 μg/kg had a significant increase in latency when compared to pre-dose.

In preferred embodiments, other compounds, including those described in commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof", filed herewith, can also be tested using the aforementioned assay.

Example 6
Effect of an alpha$_{1A}$ Adrenergic Receptor Antagonist on the Cold Allodynia Response in Neuropathic Rats This experiment was conducted as described in Example 3 to evaluate the effects of 3-(3-{4-[2-(2,2,2-trifluoroethoxy)phenyl]-piperazin-1-yl}propyl)-5-methyl-2,4(1H,3H)-pyrimidinedione, and similar or related compounds, on the cold allodynia response in neuropathic rats. 3-(3-{4-[2-(2,2,2-Trifluoroethoxy)phenyl]-piperazin-1-yl}propyl)-5-methyl-2,4(1H,3H)-pyrimidinedione was prepared as described in Example 32 of U.S. Pat. No. 5,859,014 to Bantle et al.

Male Sprague-Dawley rats (Harlan), 170–270 g, were surgically prepared to have a chronic constriction injury (CCl) as described above 14 days prior to testing. Rats were selected and tested as described in Example 3. Selected rats were dosed at 0 (vehicle, 10 mL/kg, deionized water), 30 or 300 μg/kg, i.p. After 20 min and 40 minutes post-dosing, rats were tested in the cold bath assay.

The results from this experiment indicate that when compared with changes from pre-dose, only the group receiving 3-(3-{4-[2-(2,2,2-trifluoroethoxy)phenyl]-piperazin-1-yl}propyl)-5-methyl-2,4(1H,3H)-pyrimidinedione at 300 μg/kg showed significant changes only at 40 min post-dose compared to the vehicle group.

3-(3-{4-[2-(2,2,2-Trifluoroethoxy)phenyl]-piperazin-1-yl}propyl)-5-methyl-2,4(1H,3H)-pyrimidinedione only at 300 μg/kg showed a significant increase in latency times than the vehicle control at 40 min post-dose.

In preferred embodiments, other compounds, including those described in commonly owned U.S. patent applications U.S. S.No. 60/124,781; filed on Mar. 17, 1999; U.S. S.No. 60/165,312, filed on Nov. 12, 1999; and U.S. Ser. No. 09/521,185, filed Mar. 8, 2000 by Coffen, et al. entitled "Oxazolone Derivatives and Uses Thereof", filed herewith, can also be tested using the aforementioned assay.

Example 7
Tail Flick Model

The tail-flick test (D'Amour et al. (1941) *J. Pharmacol. Exp. and Ther.* 72:74–79) is a model of acute pain. A towel-wrapped rat is placed on a test stage such that a focused light source beams on the dorsal surface of the rat's tail. A photosensor is present on the test stage located opposite the light source and below the rat's tail. To begin the test, the rat's tail blocks the light, thus preventing the light reaching the photosensor. Latency measurement begins with the activation of the light source. When a rat moves or flicks its tail, the photosensor detects the light source and stops the measurement. The test measures the period of time (duration) that the rat's tail remains immobile (latent). Rats are tested prior to administration thereto of a compound of interest and then at various times after such administration. The light source is set to an intensity that produced a tail response latency of about 3 seconds when applied to the tails of rats to which no compound has been administered.

Example 8
Rat Tail Immersion Model

The rat tail immersion assay is also a model of acute pain. A rat is loosely held in hand while covered with a small folded thin cotton towel with its tail exposed. The tip of the tail is dipped into a, e.g., 52° C. water bath to a depth of two inches. The rat responds by either wiggling of the tail or withdrawal of the tail from the water; either response is scored as the behavioral end-point. Rats are tested for a tail response latency (TRL) score prior to administration thereto of a compound of interest and then retested for TRL at various times after such administration.

Example 9
Carrageenan-induced Paw Hyperalgesia Model

The carrageenan paw hyperalgesia test is a model of inflammatory pain. A subcutaneous injection of carrageenan is made into the left hindpaws of rats. The rats are treated with a selected agent before, e.g., 30 minutes, the carrageenan injection or after, e.g., two hours after, the carrageenan injection. Paw pressure sensitivity for each animal is tested with an analgesymeter three hours after the carrageenan injection. See, Randall et al. (1957) *Arch. Int. Pharmacodyn.* 111:409–419.

The effects of selected agents on carrageenan-induced paw edema can also be examined. This test (see, Vinegar et al. (1969) *J. Phamacol. Exp. Ther.* 166:96–103) allows an assessment of the ability of a compound to reverse or prevent the formation of edema evoked by paw carrageenan injection. The paw edema test is carried out using a plethysmometer for paw measurements. After administration of a selected agent, a carrageenan solution is injected subcutaneously into the lateral foot pad on the plantar surface of the left hind paw. At three hours post-carrageenan treatment, the volume of the treated paw (left) and the un-treated paw (right) is measured using a plethysmometer.

Example 10
Formalin Behavioral Response Model

The formalin test is a model of acute, persistent pain. Response to formalin treatment is biphasic (Dubuisson et al. (1977) *Pain* 4:161–174). The Phase I response is indicative of a pure nociceptive response to the irritant. Phase 2, typically beginning 20 to 60 minutes following injection of formalin, is thought to reflect increased sensitization of the spinal cord.

Example 11
Von Frey Filament Test

The effect of compounds on mechanical allodynia can be determined by the von Frey filament test in rats with a tight ligation of the L-5 spinal nerve: a model of painful peripheral neuropathy. The surgical procedure is performed as described by Kim et al. (1992) *Pain* 50:355–363. A calibrated series of von Frey filaments are used to assess mechanical allodynia (Chaplan et al. (1994) *J. Neurosci. Methods* 53:55–63). Filaments of increasing stiffness are applied perpendicular to the midplantar surface in the sciatic nerve distribution of the left hindpaw. The filaments are slowly depressed until bending occurred and are then held for 4–6 seconds. The filament application order and number of trials were determined by the up-down method of Dixon (Chaplan et al., supra). Flinching and licking of the paw and paw withdrawal on the ligated side are considered positive responses.

Example 12
Chronic Constriction Injury

Heat and cold allodynia responses can be evaluated as described below in rats having a chronic constriction injury (CCI). A unilateral mononeuropathy is produced in rats using the chronic constriction injury model described in Bennett et al. (1988) *Pain* 33:87–107.

CCI is produced in anesthetized rats as follows. The lateral aspect of each rat's hind limb is shaved and scrubbed with Nolvasan. Using aseptic techniques, an incision is made on the lateral aspect of the hind limb at the mid-thigh level. The biceps femoris is bluntly dissected to expose the sciatic nerve. On the right hind limb of each rat, four loosely tied ligatures (for example, Chromic gut 4.0; Ethicon, Johnson and Johnson, Somerville, N.J.) are made around the sciatic nerve approximately 1–2 mm apart. On the left side of each rat, an identical dissection is performed except that the sciatic nerve is not ligated (sham). The muscle is closed with a continuous suture pattern with, e.g., 4–0 Vicryl (Johnson and Johnson, Somerville, N.J.) and the overlying skin is closed with wound clips. The rats are ear-tagged for identification purposes and returned to animal housing.

Example 13
Locomotor Activity Test

The locomotor activity test is described in, e.g., Winter, C. A., and L. Flataker, *J. Pharmacol. Exp. Therap.* 103:93–105, 1951. Rats are placed in individual plexiglass cages and allowed to move freely. The photobeam array (Photobeam Activity System, San Diego Instruments, San Diego, Calif.), comprises an infrared photobeam which is emitted by photodiodes on one side of the cage and detected by transistors on the opposite surface of the cage. The array is placed around the exterior of the cage. When an animal moves within the cage light beams are broken in succession. The infrared photobeam breaks can be recorded on a data file generated by the Photobeam Activity System software. The activity of each study animal is typically monitored every 15 seconds for 15 minutes.

Example 14
Alpha$_1$ Adrenergic Receptor In Vitro Assay in Tissue Isolated from Rabbit and Rat Thoracic aorta are isolated from rats and immediately immersed in Krebs' solution (comprising in mM concentrations: NaCl, 118.5; NaHCO$_3$, 25; dextrose, 5; KCl, 4.8; CaCl$_2$, 2.5; MgSO$_4$, 1.2; KH$_2$PO$_4$, 1.2; cocaine, 0.03; corticosterone, 0.03; propranolol, 0.001; ascorbic acid, 0.1; and indomethacin, 0.01). The aortas are dissected free from extraneous tissue and then a cross-sectional ring approximately 3 mm in length is cut from the most proximal segment. The aortic rings are suspended vertically in 10 mL tissue baths and bathed in Krebs' solution maintained at 37° C. and constantly aerated with a 95% O$_2$:5% CO$_2$ gas mixture. A resting tension (preload) of 1 g is applied to each aortic ring and thereafter periodically readjusted to maintain a 1 g resting tension throughout the duration of the assay.

Urinary bladders are emptied and isolated from rabbits. Bladders are dissected free from extraneous tissue and then a cross sectional ring of bladder neck tissue is cut above the urethra to approximately one third of the way up the bladder. The bladder neck is cut parallel to the longitudinal muscle fibers to give flat section of muscle tissue and then the flat section is cut parallel to the longitudinal muscle to give several flat strips. Strips of bladder tissue are suspended vertically in 10 mL tissue baths and bathed in Krebs' solution maintained at 33° C. and constantly aerated with a 95% O$_2$:5% CO$_2$ gas mixture. A resting tension of 5 g was applied to each urinary bladder stri.p. The strips are allowed to relax to a resting tension of 1 g and thereafter periodically readjusted to maintain the 1 g resting tension throughout the duration of the assay.

The aortic ring or urinary bladder strip preparations are allowed to equilibrate for 60 minutes during which period the bath solution is replaced every 15 minutes. The tissue is then exposed to bath solution containing norepinephrine (0.1 to 10 $\mu$M) and once a steady state contraction is produced the tissue is exposed to bath solution free of norepinephrine, replacing the solution twice every 5 minutes for 30 minutes. The aortic rings are exposed to norepinephrine and the urinary bladder strips to phenylephrine in a cumulative concentration fashion. That is, the isolated tissue is exposed to bath solution containing a threshold concentration of either norepinephrine or phenylephrine until a steady state contractile response is attained and then the concentration of agonist is cumulatively increased by 0.5 log increments until a maximal or near maximal response is attained.

The tissue is then exposed to solution free of agonist compound, replacing the solution twice every 5 minutes for 30 minutes. After baseline tension is established and readjusted to 1 g, the tissue is exposed to bath solution containing the test compound, replacing the solution every 15 minutes for 60 minutes. In the presence of the test compound, the tissue again is exposed to either norepinephrine or phenylephrine in a cumulative concentration fashion, increasing the agonist concentration until a maximal or near maximal response was achieved.

The concentration ratio (CR) of agonist necessary to produce equiactive responses in the absence and presence of the test compound is determined. Relying on the concentration ratio, the assay concentration (molar) of the test compound, and the relationship $$pKb=-\log([test\ compound]/(CR-1))$$

the negative log of the dissociation constant ($pA_2$) for each test compound at alpha$_1$-adrenergic receptors are estimated for both aortic tissue and urinary bladder tissue.

Example 15
Alpha$_1$ Adrenergic Receptor In Vitro, Functional Assay in Tissue Isolated from Human Human arterial blood vessels are obtained post-mortem and immediately immersed in cold physiological saline solution. Within 24 hours of removal, the isolated arterial tissue is placed in Krebs' solution (comprising in mM concentrations: NaCl, 118.5; NaHCO$_3$, 25; dextrose, 5; KCl, 4.8; CaCl$_2$, 2.5; MgSO$_4$, 1.2; KH$_2$PO$_4$, 1.2; cocaine, 0.03; corticosterone, 0.03; propranolol, 0.001; ascorbic acid, 0.1; and indomethacin, 0.01). The arteries are dissected free from extraneous tissue and then cut into cross-sectional rings approximately 3 mm in length. The arterial rings are suspended vertically in 10 mL tissue baths and bathed in Krebs' solution maintained at 37° C. and constantly aerated with a 95% O$_2$:5% CO$_2$ gas mixture. A resting tension (preload) of 1 to 1.5 g is applied to each ring and thereafter periodically readjusted to maintain a 1 g resting tension throughout the duration of the assay.

Human prostatic and bladder neck smooth muscle tissue is obtained following radical cystoprostatectomies or radical prostatectomies and immediately immersed in Krebs' solution. The prostatic and bladder tissue is dissected-free from extraneous tissue and then strips of tissue 0.8 to 1.2 cm in length and 3 to 5 mm in width are cut and suspended vertically in 10 mL tissue baths and bathed in Krebs' solution maintained at 37° C. and constantly aerated with a 95% O$_2$:5% CO$_2$ gas mixture. A resting tension (preload) of 0.75 to 1 g is applied to each muscle strip and thereafter periodically readjusted to maintain a 1 g resting tension throughout the duration of the assay.

The arterial ring and prostatic and bladder neck strip preparations are allowed to equilibrate for 60 minutes during which period the bath solution is replaced every 15 minutes. The tissue is then exposed to bath solution containing norepinephrine (1 to 10 $\mu$M) and once a steady state contraction is produced the tissue is exposed to bath solution free of norepinephrine, replacing the solution twice every 5 minutes for 30 minutes. The arterial ring and prostatic and bladder neck strip preparations are exposed to norepinephrine in a cumulative concentration fashion. That is, the isolated tissue is exposed to bath solution containing a threshold concentration of norepinephrine until a steady state contractile response is attained and then the concentration of norepinephrine is cumulatively increased by 0.5 log increments until a maximal or near maximal response is attained.

The tissue is then exposed to solution free of norepinephrine, replacing the solution twice every 5 minutes for 30 minutes. After baseline tension is established and readjusted to 1 g, the tissue is exposed to bath solution containing the test compound, replacing the solution every 15 minutes for 60 minutes. In the presence of the test compound, the tissue is again exposed to norepinephrine in a cumulative concentration fashion, increasing the norepinephrine concentration until a maximal or near maximal response is achieved.

The concentration ratio (CR) of norepinephrine necessary to produce equiactive responses in the absence and presence of the test compound is determined. Relying on the concentration ratio, the assay concentration (molar) of the test compound, and the relationship:

$$pKb=-\log([test\ compound]/(CR-1))$$

the negative log of the dissociation constant ($pA_2$) for each test compound at alpha$_1$-adrenergic receptors are estimated for the arterial ring and prostatic and bladder neck strip preparations.

Example 16
Rat In Vivo, Blood Pressure Assay

Normotensive or spontaneously hypertensive rats (0.25 to 0.45 kg) are fasted for 18 hours and anesthetized with ether. The right femoral vein is isolated and cannulated with a fluid-filled polyethylene cannulae for bolus administration of test substances. The right femoral artery is isolated and cannulated with a fluid-filled polyethylene cannula connected to an external pressure transducer for monitoring mean arterial blood pressure (MAP).

Following cannulation, rats are pretreated (intravenous route) with an angiotensin receptor antagonist, a beta adrenergic receptor antagonist and an alpha$_2$ adrenergic receptor antagonist as described in Blue et al. (*Br. J. Pharmacol.* 120:107P).

The rats are placed in restrainers and allowed to recover from anesthesia. Following a 30-minute period for stabilization, test compound or vehicle are administered, i.v., and blood pressure is monitored continuously for at least 4 hours post-administration.

Example 17
Rat In Vivo, Tilt-Response Assay

The following describes an in vivo assay in normotensive rats for measuring the propensity of a test compound to inhibit the reflex maintenance of basal blood pressure levels in response to vertical tilt.

Normotensive rats (0.25 to 0.45 kg) are fasted for 18 hours and anesthetized with ether. The right femoral vein is isolated and cannulated with a fluid-filled polyethylene cannulae for bolus administration of test substances. The right femoral artery is isolated and cannulated with a fluid-filled polyethylene cannula connected to an external pressure transducer for monitoring mean arterial blood pressure (MAP).

The rats are restrained in a supine position and allowed to recover from anesthesia. Following a 30-minute period for stabilization, test compound or vehicle are administered, i.v., and blood pressure is monitored continuously while the rats are tilted vertically at 30 to 60 degrees from supine at 15, 30 and 45 minutes post-administration.

Example 18
Dog In Vivo, Blood and Intraurethral Pressure Assay

The following describes an in vivo assay for measuring the relative effect of a test compound on hypogastric nerve stimulation-induced increases in intraurethral pressure and phenylephrine-induced increases in diastolic blood pressure in anesthetized dog.

Mongrel dogs (10 to 20 kg) are fasted for 12 to 18 hours and anesthetized with phenobarbital sodium (35 mg/kg, i.v.). An endotracheal tube is inserted and thereafter the lungs are mechanically ventilated with room air. The right femoral vein is isolated and cannulated with two polyethylene cannulae, one for the administration of a continuous infusion of phenobarbital sodium (5 to 10 mg/kg/hr) and the other for bolus administration of test substances. The right femoral artery is isolated and cannulated to the abdominal aorta with a fluid filled polyethylene cannula connected to an external pressure transducer for monitoring diastolic aortic pressure (DAP). The bladder is exposed via a ventral midline abdominal incision and emptied of urine through a 22 gauge needle. The bladder is cannulated through a stab incision with a water-filled balloon catheter connected to an external pressure transducer for monitoring prostatic intraurethral pressure (IUP). The right hypogastric nerve (HGN) is carefully isolated and attached to a Dastre's electrode for nerve stimulation.

The preparation is allowed to stabilize for a least 30 minutes and must have a stable basal IUP for not less than 15 minutes prior to commencement of the assay protocol. The HGN is stimulated (20–50 V, 10 Hz, 10 msec pulse train for 10 sec) to induce a measurable increase in IUP and then phenylephrine (PE) is administered by bolus injection (0.5 to 0.6 µg/kg, i.v.) to induce a measurable increase in DAP. The HGN stimulation and PE bolus injection are repeated every 5 minutes until three consecutive reproducible increases in IUP and DAP are achieved. Vehicle (0.1 to 0.3 mL/kg) is administered and 20 minutes later the HGN stimulation and PE bolus injection are repeated. Test compound is then administered and 20 minutes later the HGN stimulation and PE bolus injection are repeated. Test compound is administered approximately every 20 minutes, increasing the dose until maximal or near maximal inhibition of the increases in IUP and DAP is attained.

Example 19
Formulations

The following are representative pharmaceutical formulations containing a compound identified as a selective $alpha_{1B}$ adrenergic receptor antagonist by the method disclosed and claimed herein.

Tablet Formulation

The following ingredients are mixed intimately and pressed into single scored tablets.

| Ingredient | Quantity per tablet (mg) |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per tablet (mg) |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| colorings | 0.5 mg |
| distilled water | q.s. to 100 mL |

Injectable Formulation

The following ingredients are mixed to form an injectable formulation.

| Ingredient | Amount |
| --- | --- |
| compound of this invention | 0.2 g |
| sodium acetate buffer solution, 0.4 M | 2. mL |
| HCl (1 N) or NaOH (1 N) | q.s. to suitable pH |
| water (distilled, sterile) | q.s. to 20 mL |

Topical Formulation

A topical formulation is prepared with the following ingredients:

| Ingredient | Amount (g) |
| --- | --- |
| compound of this invention | 10 |
| Span 60 | 2 |
| TWEEN ®60 | 2 |
| mineral oil | 5 |
| petrolatum | 5 |
| methyl paraben | 0.15 |
| propyl paraben | 0.05 |
| BHA (butylated hydroxy anisole) | 0.01 |
| distilled water | q.s. to 100 mL |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
| --- | --- |
| compound of this invention | 500 mg |
| Witepsol ® H-15 | balance |

Nasal Spray Formulation

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–10 hours.

Although preferred embodiments of the subject invention have been described in some detail, it is understood that obvious variations can be made without departing from the spirit and the scope of the invention as defined by the appended claims.

What is claimed is:

1. A method of treating a subject to produce analgesia comprising administering to a subject in need of analgesia a therapeutically effective amount of a compound that is a selective antagonist of $alpha_{1B}$ adrenergic receptor activity, or a pharmaceutically acceptable salt or hydrate thereof and a pharmaceutically acceptable carrier, wherein said compound does not substantially antagonize $alpha_{1A}$ or $alpha_{1D}$ adrenergic receptors.

2. A method of treating a subject to produce analgesia, comprising administering to a subject in need of analgesia a therapeutically effective amount of a composition comprising a compound that is a selective antagonist of $alpha_{1A}$ or $alpha_{1B}$ adrenergic receptor activity, or a pharmaceutically acceptable salt or hydrate thereof and a pharmaceutically acceptable carrier, wherein said compound does not substantially antagonize $alpha_{1A}$ or $alpha_{1D}$ adrenergic receptors.

3. The method of claim 1, wherein said compound is identified by measuring a functional and selective $alpha_{1B}$-adrenergic receptor antagonist activity of the test compound, or a pharmaceutically acceptable salt or hydrate thereof.

4. The method of claim 2 wherein said compound is identified by measuring a functional and selective $alpha_{1B}$-adrenergic receptor antagonist activity of the test compound, or a pharmaceutically acceptable salt or hydrate thereof and a pharmaceutically acceptable carrier.

5. The method of claim 2, wherein the composition further comprises one or more compounds having at least one of anti-inflammatory activity, analgesic activity, or anticonvulsant activity.

6. The method of claim 4, wherein the composition further comprises one or more compounds having at least one of anti-inflammatory activity, analgesic activity, or anticonvulsant activity.

7. The method of claim 1, wherein said compound is identified by a method comprising:

a) measuring the activity of a test compound in a first binding assay, comprising i) providing a preparation of a cell that expresses an $alpha_{1B}$ adrenergic receptor, ii) combining the test compound with the cell preparation, iii) measuring binding of the test compound to the cell preparation or the receptor;

b) measuring activity of the test compound in at least one pain model;

c) measuring the activity of the test compound in a second binding assay, comprising i) providing a preparation of a cell that expresses an $alpha_{1A}$ adrenergic receptor, a preparation of a cell that expresses an $alpha_{1D}$ adrenergic receptor, or a preparation of a cell that expresses an $alpha_{1A}$ adrenergic receptor and a preparation of a cell that expresses an $alpha_{1D}$ adrenergic receptor, ii) combining the test compound with the cell preparation, and iii) measuring the binding of the test compound to the cell or the receptor;

wherein (a), (b), and (c) are done concurrently or consecutively in any order; and d) selecting a compound that is a selective antagonist of $alpha_{1B}$ receptor activity.

8. The method of claim 2, wherein said compound is identified by a method comprising:

a) measuring the activity of a test compound in a first binding assay, comprising i) providing a preparation of a cell that expresses an $alpha_{1B}$ adrenergic receptor, ii) combining the test compound with the cell preparation, iii) measuring binding of the test compound to the cell preparation or the receptor;

b) measuring activity of the test compound in at least one pain model;

c) measuring the activity of the test compound in a second binding assay, comprising i) providing a preparation of a cell that expresses an $alpha_{1A}$ adrenergic receptor, a preparation of a cell that expresses an $alpha_{1D}$ adrenergic receptor, or a preparation of a cell that expresses an $alpha_{1A}$ adrenergic receptor and a preparation of a cell that expresses an $alpha_{1D}$ adrenergic receptor, ii) combining the test compound with the cell preparation, and iii) measuring the binding of the test compound to the cell or the receptor;

wherein (a), (b), and (c) are done concurrently or consecutively in any order; and d) selecting a compound that is a selective antagonist of $alpha_{1B}$ receptor activity.

9. The method of claim 1, wherein neuropathic pain is reduced.

10. The method of claim 1, wherein acute pain is reduced.

11. The method of claim 1, wherein inflammatory pain is reduced.

12. The method of claim 2, wherein neuropathic pain is reduced.

13. The method of claim 2, wherein acute pain is reduced.

14. The method of claim 2, wherein inflammatory pain is reduced.

* * * * *